United States Patent
Seppi et al.

(10) Patent No.: US 7,289,599 B2
(45) Date of Patent: Oct. 30, 2007

(54) RADIATION PROCESS AND APPARATUS

(75) Inventors: Edward J. Seppi, Portola Valley, CA (US); John Pavkovich, Palo Alto, CA (US)

(73) Assignee: Varian Medical Systems Technologies, Inc., Palo Alto, CA (US)

(*) Notice: Subject to any disclaimer, the term of this patent is extended or adjusted under 35 U.S.C. 154(b) by 323 days.

(21) Appl. No.: 10/656,438

(22) Filed: Sep. 5, 2003

(65) Prior Publication Data

US 2004/0096033 A1    May 20, 2004

Related U.S. Application Data

(60) Provisional application No. 60/416,022, filed on Oct. 4, 2002.

(51) Int. Cl.
*A61N 5/10* (2006.01)
(52) U.S. Cl. .................................... 378/65
(58) Field of Classification Search ............ 378/5, 378/65, 56, 90, 62, 64, 68, 119, 121
See application file for complete search history.

(56) References Cited

U.S. PATENT DOCUMENTS

| | | | |
|---|---|---|---|
| 4,361,901 A * | 11/1982 | Daniels et al. ............ 378/106 |
| 5,099,846 A | 3/1992 | Hardy ....................... 600/407 |
| 5,464,013 A * | 11/1995 | Lemelson ................... 378/65 |
| 5,548,627 A | 8/1996 | Swerdloff et al. |
| 5,661,773 A * | 8/1997 | Swerdloff et al. ........... 378/65 |
| 5,751,781 A | 5/1998 | Brown et al. |
| 6,055,295 A * | 4/2000 | Murthy et al. ............. 378/151 |
| 6,122,341 A | 9/2000 | Butler et al. ................ 378/20 |
| 6,167,296 A | 12/2000 | Shahidi ..................... 600/427 |
| 6,405,072 B1 | 6/2002 | Cosman |
| 6,459,762 B1 | 10/2002 | Wong et al. |
| 6,459,769 B1 | 10/2002 | Cosman |
| 6,618,467 B1 * | 9/2003 | Ruchala et al. ............. 378/65 |
| 6,735,277 B2 * | 5/2004 | McNutt et al. .............. 378/65 |
| 6,799,670 B1 | 10/2004 | Korecki .................... 194/302 |
| 6,842,502 B2 | 1/2005 | Jaffray et al. |
| 2002/0150207 A1 * | 10/2002 | Kapatoes et al. ........... 378/65 |
| 2003/0048868 A1 * | 3/2003 | Bailey et al. ............... 378/65 |

(Continued)

FOREIGN PATENT DOCUMENTS

EP          205720 A1 * 12/1986

OTHER PUBLICATIONS

International Search Report dated May 7, 2004.

(Continued)

*Primary Examiner*—Courtney Thomas
(74) *Attorney, Agent, or Firm*—Bingham McCutchen LLP

(57) ABSTRACT

A radiation apparatus (10) includes a beam source (12) generating radiation beam toward a target (11). A projection detector (17) detects the images of the target (11) formed by the radiation beam. In a radiation treatment session using the apparatus (10), the beam source (12) first generates a low intensity beam. The projection detector (17) generates image signals of a patient under the treatment. A control module (18) in the apparatus (10) develops a treatment plan in accordance with a treatment prescription and the image signals. Subsequently, the beam source (12) generates a treatment beam according to the treatment plan. The projection detector (17) can generate further image signals formed by the treatment beam to verify the treatment process.

55 Claims, 6 Drawing Sheets

U.S. PATENT DOCUMENTS

2004/0049109 A1    3/2004    Thornton .................... 600/427
2004/0114718 A1    6/2004    Brown

OTHER PUBLICATIONS

Jaffray, D.A. et al. "A Radiographic and Tomographic Imaging System Integrated into a Medical Linear Accelerator for Localization of Bone and Soft-Tissue Targets" *Int. J. Radiation Oncology Biol. Phys.* (1999) 45(3):773-789.

Haworth, A. et al. "Registration on Prostate Volume with Radiographically Identified Iodine-125 Seeds for Permanent Implant Evaluation" Journal of Brachytherapy International, vol. 16, No. 3, Jul.-Sep. 2000, pp. 157-167.

* cited by examiner

RADIATION PROCESS AND APPARATUS

RELATED APPLICATION DATA

This application claims priority to U.S. Provisional Patent Application No. 60/416,022, filed on Oct. 4, 2002, the entire disclosure of which is expressly incorporated by reference herein.

BACKGROUND OF THE INVENTION

The present invention relates generally to a system and method of providing radiation treatment, and in one embodiment, specifically to a system and method for cone beam real time radiation treatment and optimization.

Various systems and methods exist to provide radiation therapy treatment of tumorous tissue with high-energy radiation. While some patient conditions require whole body radiation treatments, many forms of radiation treatment benefit from the ability to accurately control the amount, location and distribution of radiation within a patient's body. Such control often includes applying various levels of radiation to various areas of the tumorous region. For example, in some instances it is desirable to apply a greater dosage of radiation to the interior portion of a tumorous region than to the exterior portions of the region. As another example, in some instances it is desirable to minimize the dosage of radiation to non tumorous regions where radiation may have deleterious effects. Due to a variety of contributing factors, achieving accurate control of the amount, location and distribution of radiation within the patient's body can be difficult. Among these factors are movement in the patient's body, changes in organ or inter organ structure or composition, and changes in the relative position of a patient's organs.

Prior to a radiation therapy, the patient undergoes extensive imaging procedures to determine the exact size, shape and location of the tumorous region. The radiation therapy typically includes a plurality of radiation sessions over a period of several weeks. In a radiation session, the patient is subjected to radiation from an accelerator that emits a beam of radiation energy collimated and oriented to entry the patient's body from a particular angle. Varying the intensity and the entry angle of the incident radiation beam allows radiation specialist to generate a radiation dose volume that corresponds to the size, shape, and location of the tumorous region.

Several factors may prevent optimal radiation exposure to the tumorous region and minimal radiation exposure of the healthy tissue regions. For example, movement as minor as those attributable to the patient breathing may affect radiation dosages. Minor changes in patent's position from the imaging gantry to the treatment gantry may radically alter the position of the tumorous region or organ. The size, shape, or location of the tumor may change between the radiation treatment sessions. In addition, varying degrees of tissue density and radiation attenuation characteristics may have a dramatic effect upon the effectiveness and accuracy of a dosage prescription.

Accordingly, it would be advantageous to have an apparatus and a method for a radiation therapy, wherein the quality of which is not significantly affected by such factors as changes in patient anatomy, improper patient positioning and movement. It is desirable for the apparatus and the method to provide an accurate radiation dosage to the tumorous region in a patient and to minimize the radiation exposure of the healthy regions of the patient under the radiation therapy. It would be of further advantage for the apparatus and the method to be able to ensure consistently high quality of the radiation therapy.

SUMMARY OF THE INVENTION

An aspect of an embodiment of the present invention is to provide an apparatus and a method for performing an optimal quality radiation therapy. Another aspect of an embodiment of the present invention is to provide an accurate radiation dosage to a target regions, while minimizing the radiation exposure of the surrounding regions. Another aspect of an embodiment of the present invention is to perform the radiation therapy so that its quality is not significantly affected by such factors as improper patient positioning, patient movement, patient condition changes, or inadequately optimized planning.

In accordance with one embodiment of the present invention, real time radiation treatment planning is performed before delivering radiation to a patient. Such process provides an accurate and precise dosage of radiation to a patient. The planning process acquires configuration data and radiation absorption data, and generates a radiation treatment plan in response thereto. By means of non-limiting examples, the configuration data may include one or a combination of location, size, and shape of a target object. In another embodiment, a low dose plan verification can be applied for verification of the treatment plan. Changes to the plan for further optimization can be developed. When the plan is fully optimized a full dose radiation delivery may be performed and the desired radiation dosage is delivered to the patient according to the radiation treatment plan. In another embodiment, the distribution and magnitude of the delivered dose can be verified.

In accordance with another embodiment of the present invention, the radiation treatment planning, radiation delivery, and verification processes are performed in a single radiation treatment session with the patient staying on the same platform. This real time planning minimizes the effect of tumor and anatomy configuration changes between the treatment sessions and the effect of patient positioning on the radiation delivery. In one embodiment, the real time planning process includes irradiating the patient with a low energy X-ray image beam for generating configuration image and a high energy, low intensity radiation beam for generating radiation absorption data. In another embodiment, radiation plan verification can be performed during the radiation delivery process.

An apparatus for irradiating an object is provided in accordance with an embodiment of the present invention. The apparatus includes a platform for supporting an object, and a first beam source for generating a first radiation beam at a first intensity level and a second radiation beam at a second intensity level toward the platform. The apparatus also includes a projection detector for generating a first image of the object illuminated by the first radiation beam at the first intensity level. A beam adjuster may be provided and positioned in front of the first beam source, and a control module may be coupled to the projection detector and to the beam adjuster. In one embodiment, the apparatus further includes a second beam source for generating an image beam toward the platform. In this case, the projection detector is also configured to generate a second image of the object illuminated by the image beam. The control module can develop a radiation treatment plan based on one or both of the first and second images. In another embodiment, the control module adjusts one or a combination of a shape, an intensity, and a direction of a radiation beam.

Systems for performing radiation process are also provided. Other aspects and features of the invention will be evident from reading the following detailed description of the preferred embodiments, which are intended to illustrate, not limit, the invention.

DETAILED DESCRIPTION OF VARIOUS EMBODIMENTS

Figure 1:
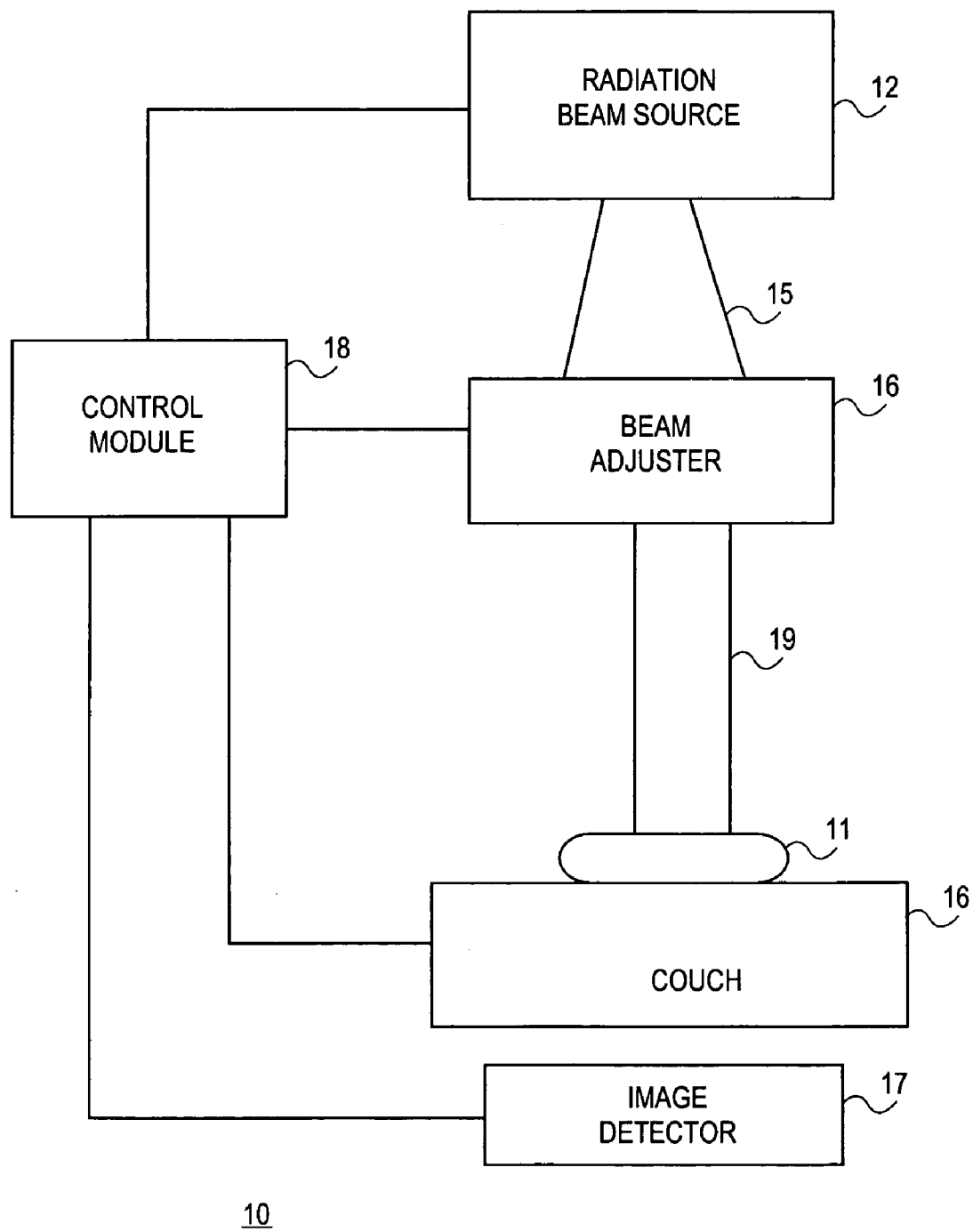
FIG. 1 is a functional block diagram of a radiation treatment apparatus in accordance with an embodiment of the present invention.

Various embodiments of the present invention are described hereinafter with reference to the figures. It should be noted that the figures are not drawn to scale and elements of similar structures or functions are represented by like reference numerals throughout the figures. It should also be noted that the figures are only intended to facilitate the description of specific embodiments of the invention. They are not intended as an exhaustive description of the invention or as a limitation on the scope of the invention. In addition, an illustrated embodiment needs not have all the aspects or advantages of the invention shown. An aspect or an advantage described in conjunction with a particular embodiment of the present invention is not necessarily limited to that embodiment and can be practiced in any other embodiments of the present invention even if not so illustrated.

FIG. 1 is a functional block diagram illustrating a radiation treatment apparatus 10 in accordance with an embodiment of the invention. Apparatus 10 includes a radiation beam source 12. By way of example, radiation beam source 12 generates an X-ray beam 15 toward a couch or platform 14. A beam adjuster 16 in front of beam source 12 functions to adjust the shape, size, intensity, and direction of a beam 19 reaching a patient 11 on platform 14 during a radiation treatment session. In a specific embodiment, beam adjuster 16 includes one or more multiple leaf collimators. In an alternative embodiment, beam adjuster 16 includes one or more multiple leaf collimators and one or more single jaw collimators. Apparatus 10 also includes a control module 18 coupled to beam source 12, platform 14, and beam adjuster 16 to control their operations. In addition, apparatus 10 includes a projection detector 17 coupled to control module 18. By way of example, projection detector 17 is an X-ray detector.

Beam source 12 is capable of generating radiation beams at different energy levels. Beam source 12 may include a single beam generation module or multiple beam generation modules. In accordance with a specific embodiment of the present invention, beam source 12 is configured to generate X-ray radiation beams at a kilo-electron-volt (keV) energy level and a mega-electron-volt (MeV) energy level. A keV energy level X-ray radiation beam is generally used for forming images of the tumor and/or tissues in patient 11, and is therefore also referred to as an image beam or a diagnostic beam. An MeV energy level X-ray radiation beam is generally used for treating a tumor or other abnormal tissue in patient 11. The MeV energy level X-ray radiation beam can also be used for forming images of patient 11. However, images formed using an MeV energy level X-ray beam typically have lower contrast and spatial resolutions than those formed with an X-ray beam at a lower energy level, e.g., keV energy level. In accordance with one embodiment of the present invention, beam source 12 includes two X-ray beam generators, one for generating the keV energy level X-ray image beams and another for generating the MeV energy level X-ray radiation beams. The two beam generators may be located in close proximity with each other or separated from each other. For example in one specific embodiment, the two beam generators are so located that they project radiation beams toward the patient on platform 14 at an angle of approximately 90° from each other. In accordance with another embodiment, beam source 12 includes a signal X-ray beam generator that is capable of generating X-ray beams at multiple energy levels. By way of example, U.S. patent application Ser. No. 10/033,327 entitled "RADIOTHERAPY APPARATUS EQUIPPED WITH AN ARTICULABLE GANTRY FOR POSITIONING AN IMAGING UNIT" and filed on Nov. 2, 2001 discloses a system with X-ray radiation sources at different energy levels. U.S. patent application Ser. No. 10/033,327 is incorporated herein by reference in its entirety.

Projection detector 17 is capable of detecting images of the tumor and surrounding tissues in patient 11 formed by the X-ray beams at both the MeV high energy level and the keV low energy level. In accordance with one embodiment, projection detector 17 includes two image detecting devices, one for detecting images formed by the keV image beams, and the other for detecting images formed by the MeV radiation beams. In accordance with another embodiment, projection detector 17 includes a single image detecting device that is capable of detecting images formed by beams at multiple energy levels. By way of example, U.S. patent application Ser. No. 10/013,199 entitled "X-RAY IMAGE ACQUISITION APPARATUS" and filed on Nov. 2, 2001 discloses an X-ray image detecting device that is capable of detecting multiple energy level X-ray images and can be used as projection detector 17 in accordance with the present invention. U.S. patent application Ser. No. 10/013,199 is incorporated herein by reference in its entirety.

In accordance with one embodiment of the present invention, control module 18 includes a signal processor such as, for example, a digital signal processor (DSP), a central processing unit (CPU), or a microprocessor (μP), and a memory coupled to the signal processor. Control module 18 may also include multiple signal processors working in unison to achiever a high signal processing speed. The memory serves to store a radiation treatment prescription prescribed by an oncologist for patient 11. The memory also serves to store a treatment plan for patient 11 developed in accordance with the present invention as described herein below and other programs for the operation of apparatus 10. The signal processor in control module 18 executes the programs and generates signals for the operation of beam source 12, platform 14, beam adjuster 16, and projection detector 17.

It should be noted that apparatus 10 in accordance with the present invention is not limited to having the structure as describe herein above. For example, beam source 12 is not limited to generating X-ray radiation at the keV and MeV energy levels. Depending on the nature of treatment or application, radiation beam source 12 may generate X-ray radiation at other energy spectrums or generate other kinds of radiation beams, which include, but are not limited to, beta ray beams, positron beams, proton beams, antiproton beams, neutron beams, heavy ion beams, e.g., alpha ray beams, carbon ion beams, etc. Projection detector 17 may include different kinds of radiation sensors corresponding to different radiation beam sources. Further, apparatus 10 is not limited to having one projection detector 17 as shown in FIG. 1. In alternative embodiments, apparatus 10 may include two or more image detectors. For example, multiple image detectors can be used for providing stereotactic image data.

Figure 2:
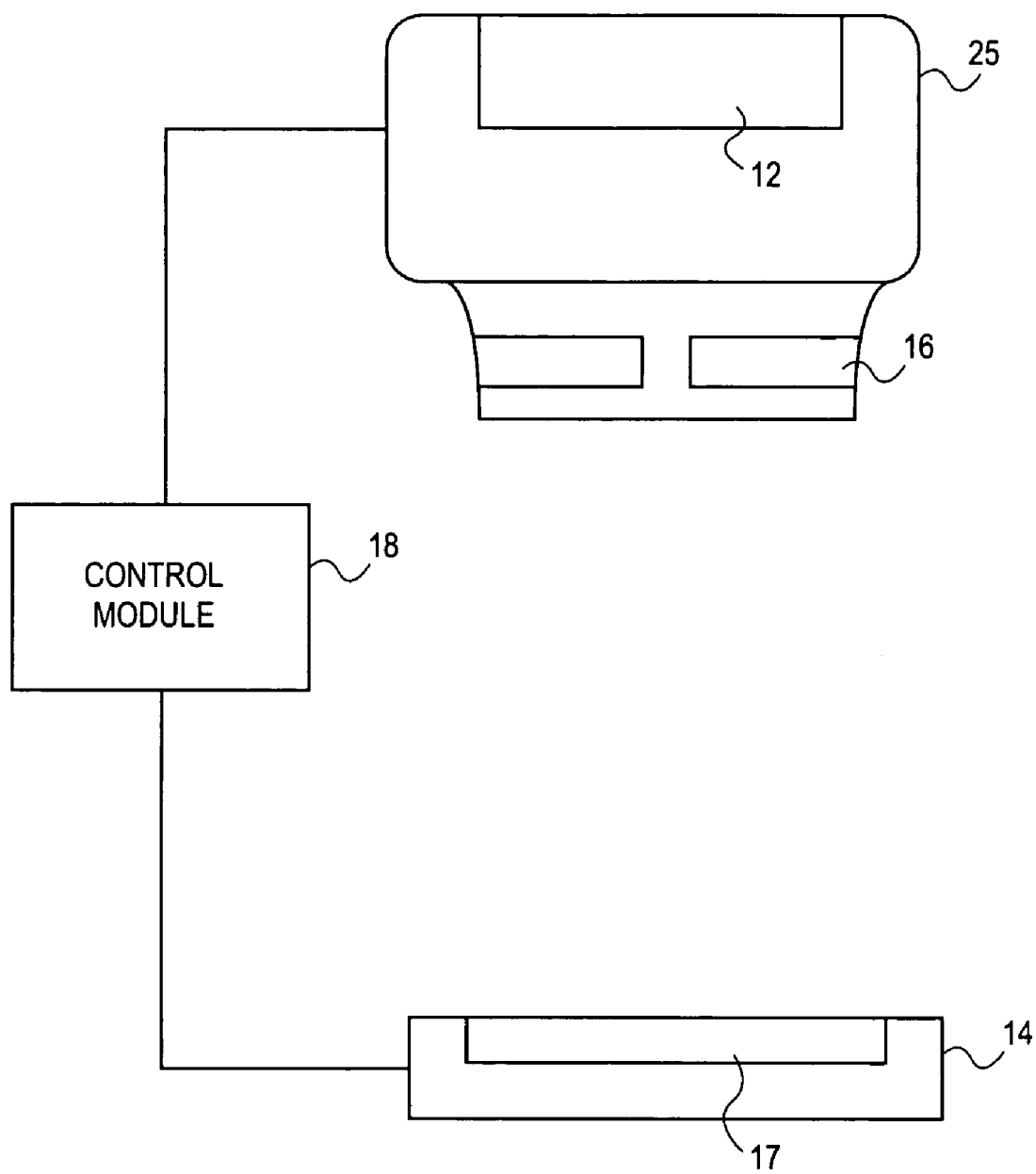
FIG. 2 schematically illustrates a radiation treatment apparatus in accordance with an embodiment of the present invention.

FIG. 2 is a schematic diagram illustrating a radiation therapy apparatus 20 in accordance with an embodiment of the present invention. The functional structure of apparatus 20 is similar to that of apparatus 10 described herein above with reference to FIG. 1. Apparatus 20 includes a gantry 25 positioned over platform or couch 14 and housing radiation source 12 and beam adjuster 16. In a preferred embodiment, gantry 25 is capable of rotating around platform 14 so that the radiation beam generated by radiation source 12 can be projected onto a patient on couch 14 from different directions. Apparatus 20 also includes a projection detector 17 mechanically coupled to (not shown in FIG. 2) gantry 25. A control module 18 controls the operation of apparatus 20.

In operation, control module 18 processes the image signals from projection detector 17 to calculate the data regarding the position, shape, density, and/or size of the tumor and the surrounding tissues the patient. Control module 18 may also process the image signals to calculate the data regarding any bolus materials surrounding the tumor in the patient that may intercept the radiation treatment beam. These data are used to generate beam adjustment signals to control beam adjuster 16, thereby adjusting the position of the radiation beam projected on the patient. In alternative embodiments, the beam adjustment signals can also control gantry 25 for changing beam position and/or control couch 14 for repositioning the patient. In general, any combination of the movements of beam adjuster 16, gantry 25, and couch 14 may be used to cause the radiation beam tracking the movement of target. Accordingly, discussion of any mode of target tracking herein does not preclude use of other modes in addition to the mode under discussion. The control module 18 can additionally be used for switching the radiation beam on and off for intensity control or in a gating process.

In an alternative embodiment, apparatus 20 includes an image beam source separated from radiation beam source 12. The separate image beam source may be mechanically coupled to gantry 25. Alternatively, the image beam sources can be mounted on the ceiling of a treatment room, in which apparatus 20 is installed. Likewise, projection detector 17 can be mounted on couch 14 or in the floor of the treatment room.

In order to provide accurate and reliable radiation treatment to a patient, radiation treatment apparatus 10 shown in FIG. 1 and apparatus 20 shown in FIG. 2 are preferably calibrated to maintain the accuracy, proper function, and desirable working states of various components in the apparatuses. In accordance with one embodiment of the present invention, the calibration is performed each time before an apparatus is used for a radiation treatment session. The calibration can also be performed from time to time on a more or less regular basis. In one alternative embodiment, the apparatus can be calibrated on a regular time basis such as, for example, calibrated once a week, or once a month. In another alternative embodiment, the apparatus is calibrated on a usage basis such as, for example, calibrated once after performing ten radiation treatment sessions or fifty radiation treatment sessions. By way of example, the calibration is performed using phantoms such as, e.g., cylindrical water phantoms, phantoms with anatomy structure and composed of tissue equivalent materials, etc. A calibration phantom provides a reference radiation absorption rate for calibrating apparatus 10 or 20.

To perform the calibration in accordance with an embodiment of the present invention, a phantom is placed on platform 14. In accordance with an aspect of the present invention, the dimension and geometry of the phantom are known. Therefore, the absorption rates of the radiation projected on the phantom from different directions can be determined. An estimated treatment plan for a radiation treatment session can be generated to define radiation beam intensity profiles, directions, and other properties to achieve a particular dose and dose distribution with the phantom. Beam source 12 is switched on to generate a radiation beam at a predetermined energy level, which may be referred to as an incident beam energy, and a predetermined intensity. Control module 18 adjusts the energy and intensity and shape of the beam projected from beam source 12 and records the beam energy and intensity profile.

When the estimated treatment plan is applied to the phantom, one or more radiation detectors (not shown in the figures) measure the actual radiation dose distribution data. The actual radiation dose distribution data is combined with the dose distribution data obtained through projection detector 17 to calibrate radiation treatment apparatus 10. In a specific embodiment, the dose distribution data are collected while beam adjuster 16 is wide open and does not block any of the radiation from beam source 12. Control module 18 calculates the dose line integrals by summing the dose distribution along the beam ray lines. In accordance with an embodiment of the present invention, a dose line integral is calculated for each beam incident direction by summing the radiation dose distribution data along the beam ray line. From the dose line integrals, control module 18 calculates the volume dose distribution resulting from the "treatment" of the phantom. In another specific embodiment, the dose line integrals are calculated for a cone shaped beam generated by beam source 12 with a maximum beam aperture. In this embodiment, the boundary of the cone shaped beam is indicated by the dose line integrals falling to zero. From the dose line integrals, control module 18 calculates the total radiation energy deposition in the phantom, which represents the total radiation dose received by the phantom. The volume dose distribution can be constructed through back projection in a manner similar to that used in cone beam image reconstruction.

The dose distribution data, the line integral data, and the total energy deposition data are then used to calibrate various components in apparatus 10. In one embodiment of the present invention, the data are used for calibrating the sensitivity of projection detector 17 to the radiation beams. In another embodiment, the data are used for calibrating the energy and intensity levels of the beams generated in beam source 12. In yet another embodiment, the data are used for calibrating beam adjuster 16, which may be a multiple leaf collimator, and the motion of gantry 25 (shown in FIG. 2). In accordance with various embodiments of the present invention, a calibration process may calibrate a single component or several components in apparatus 10 or apparatus 20.

Figure 3:
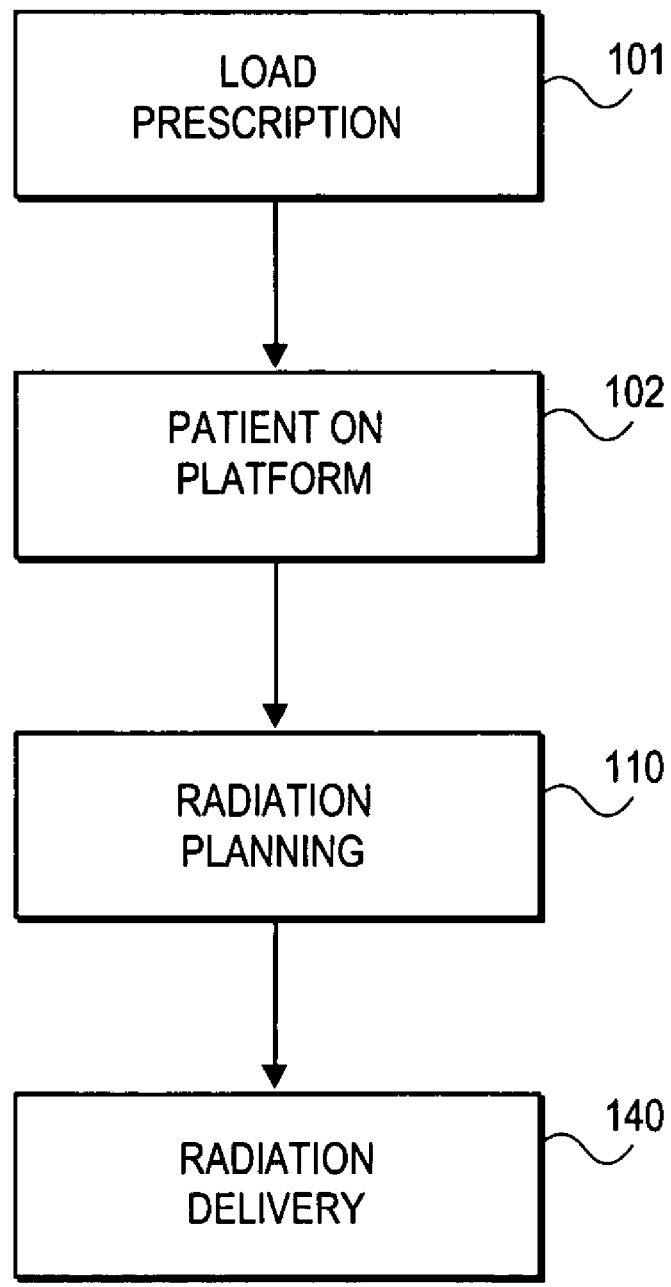
FIG. 3 is a flow chart illustrating a radiation treatment session in accordance with an embodiment of the present invention.

FIG. 3 is a flow chart illustrating a radiation treatment session 100 in accordance with an embodiment of the present invention. By way of example, radiation treatment session 100 uses a radiation treatment apparatus like apparatus 10 or 20 described herein above with reference to corresponding FIG. 1 or 2 for treating patient 11 with tumor. Also by way of example, radiation treatment session 100 is performed in accordance with a radiation treatment prescription prescribed by an oncologist for patient 11. In a step 101, the radiation treatment prescription is loaded into control module 18. Calibration information appropriate for optimizing the treatment process to achieve the prescription dose is also loaded to control module 18.

In a step 102, patient 11 is placed on platform 14. The movement of patient 11 on platform 14 is preferably minimized during radiation process 100. This can be achieved by using some restraining devices (not shown) to confine the movement of patient 11. Radiation treatment session 100 further includes a radiation treatment planning process 110 and a radiation delivery process 140.

Figure 4:
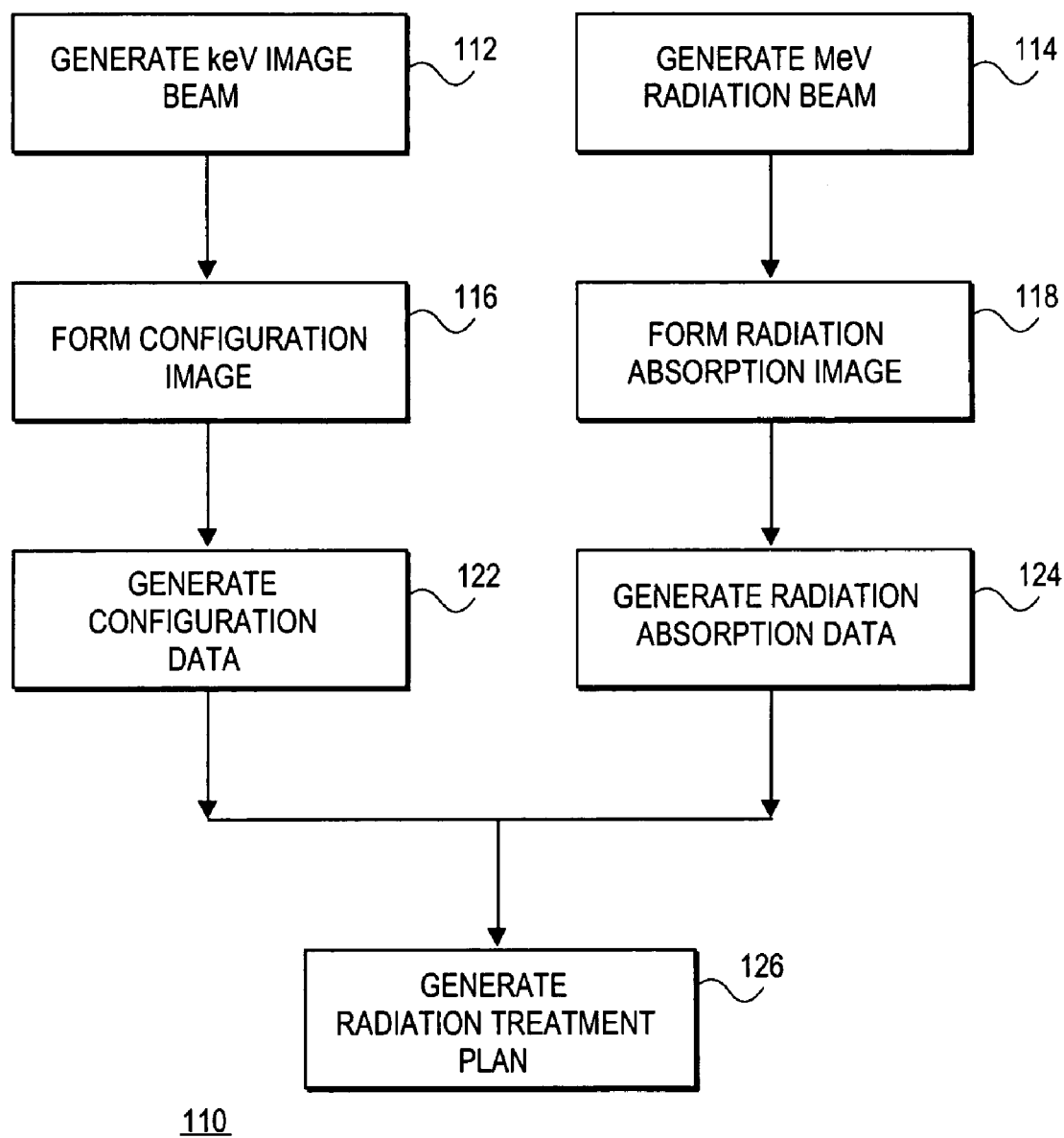
FIG. 4 illustrates a radiation treatment planning process in accordance with an embodiment of the present invention.

FIG. 4 is a flow chart illustrating a radiation treatment planning process 110 in accordance with an embodiment of the present invention. With patient 11 on platform 14, beam source 12 is switched on to generate an image beam in a step 112 and generate a low intensity radiation beam in a step 114. By way of example, the image beam is at a keV energy level and the radiation beam is at an MeV energy level. The intensities of the image beam generated in step 112 and the radiation beam generated in step 114 are preferably sufficiently low so that they have minimum effects on the total radiation dose received by patient 11. In accordance with an embodiment of the present invention, the intensity of the image beam is between approximately 1 Rad and 20 Rad, and the intensity of the radiation beam is between approximately 250 Rad and 1000 Rad.

In accordance with one embodiment of the present invention, the radiation beam generated in step 114 has a constant low intensity. In accordance with another embodiment, control module 18 modulates the intensity of the MeV radiation beam generated in step 114 of generating the low intensity MeV radiation beam. Modulating the radiation beam intensity can be achieved by adjusting beam adjuster 16, adjusting the power output of radiation source 12, or a combination of the both. Adjusting beam direction can be achieved by angular rotation of gantry 25, rotation translation and adjustment of platform 14, or a combination of both. In one aspect, the intensity of the MeV energy level radiation beam is adjusted according to the radiation treatment prescription. In one specific aspect, the intensity may be adjusted to be in proportion to the radiation dose prescribed in the radiation treatment prescription. In another specific aspect, the intensity may be adjusted to be in proportion to the radiation intensities at different beam incident directions optimized to deliver the prescribed radiation treatment. In yet another specific aspect, the intensity of the MeV radiation beam is adjusted in response to both the radiation dose and radiation intensities at various incident directions prescribed in the radiation treatment prescription.

The keV energy level image beam generated in step 112 and the MeV energy level radiation beam generated in step 114 illuminate patient 11. They partially pass through patient 11 and reach projection detector 17. In a step 116, projection detector 17 forms an image of the tissues in patient 11 formed by the keV image beam. In a step 118, projection detector 17 forms an image of the tissue in patient 11 formed by the MeV radiation beam.

In accordance with one embodiment, steps 112 and 114 generate the image beam and the radiation beam in alternating pulses. By way of example, the duration of the pulses may range between 1 microseconds (μs) and 20 μs. The pulse rate ranges, by way of example between approximately 40 pulses per second and approximately 400 pulses per second. Accordingly, projection detector 17 alternately generates images signal of the images formed by the keV image beam and the MeV radiation beam in corresponding steps 116 and 118. The images formed by the keV image beam generally has a high resolution compared with the images formed by the MeV radiation beam. Therefore, the images formed by the keV image beam are suitable for determining the configuration, e.g., location, size, and shape, of various tissues, including the tumor to be treated under the radiation treatment session 100, in patient 11. These images are also referred to as keV images or configuration images. On the other hand, the images formed by the MeV radiation beam in step 118 are suitable for calculating the radiation absorption rates of various tissues in patient 11 because the MeV radiation beam is at the same energy level as the radiation beam for treating the tumor in patient 11 as described herein after. These images are also referred to as MeV images or radiation absorption images.

In a step 122, control module 18 processes the configuration image signals. Particularly, control module 18 compares the configuration image signals with the data regarding the configuration of the tumor and surrounding tissues in patient 11 specified in the treatment prescription and stored in a memory element in control module 18. In a step 124, control module 18 calculates the absorption rates of different parts of patient 11 in response to the radiation absorption images.

In a step 126, control module 18 generates a radiation treatment plan for patient 11. Specifically, in response to the configurations and radiation absorption rates of different portions of patient 11, control module 18 modifies the incident direction and shape of the radiation treatment beam prescribed in the radiation treatment prescription. In accordance with one embodiment calibration data is used by the control module in determination of the treatment plan. In accordance with the radiation dose prescribed in the treatment prescription and radiation absorption rate data, control module 18 further generates data regarding the intensity and duration of the radiation treatment beam. Preferably, the radiation plan will enable a radiation treatment process to deliver desirably amounts of radiation to the tumor in patient 11 and minimizing the adverse effects of the radiation exposure in surrounding tissues.

Radiation treatment planning process 110 generates a treatment plan in accordance with the radiation treatment prescription and in response to the keV configuration images and the MeV radiation absorption images and the calibration data. Specifically, radiation treatment planning process 110 uses the data related to the configuration of the tumor and surrounding tissues in patient 11 and the data related to the radiation absorption rates of the tumor and surrounding tissues in patient 11 to modify the treatment prescription, thereby precisely delivering the desirable amount of radiation dose to the tumor and minimizing the adverse effects of the radiation on tissues surrounding the tumor. The radiation treatment plan is optimized through analyzing the data, e.g., radiation treatment prescription, data related to the characteristics of apparatus 10, data collected during the calibration process, etc. loaded into control module 18 and the data collected using projection detector 17 during planning process 110 to provide desirable radiation dose to different portions in the body of patient 11.

It should be understood that radiation treatment planning process 110 is not limited to what described herein above with reference to FIG. 4. For example, the keV image beam and the low density MeV radiation beam are not limited to being generated in alternating pulses. In accordance with an alternative embodiment of the present invention, step 112 of generating the keV image beam and step 114 of generating the low density MeV radiation beam are performed sequentially. First, the keV image beam is generated in step 112 and projected onto patient 11 from a plurality of directions. For example, gantry 25 (shown in FIG. 2) housing beam source 12 and beam adjuster 16 rotates around platform 14 while generating the keV image beam. Projection detector 17 generates, in step 116, a plurality of configuration images of patient 11 formed by the keV image beam from different directions. Subsequently, the low density MeV radiation beam is generated in step 114 with the gantry rotating around platform 14. Projection detector 17 generates, in step 118, a plurality of radiation absorption rate images formed by the MeV radiation beam from different directions. In this embodiment, the intensity and projection direction of the MeV radiation beam generated in step 114 can be modulated in response to the configuration images generated in step 116 as well as in accordance with the radiation treatment prescription. Furthermore, projection detector 17 can be changed between step 116 of generating the configuration images and step 118 of generating the radiation absorption rate images. Thus, an image detector sensitive to the keV image beam can be used in step 116, and a different image detector sensitive to the MeV radiation beam can be used in step 118.

In accordance with another alternative embodiment of the present invention, control module 18 first sets the beam adjuster 16 open to collect data for image beam and radiation beam reconstruction. Control module 18 then adjusts beam adjuster 16 in accordance with the radiation treatment prescription and the beam reconstruction data and generates data regarding the radiation absorption rates of the tumor and surrounding tissues in patient 11. A radiation treatment plan that best conforms to the prescribed dose and dose distribution is thereby generated using the beam construction data and radiation absorption rate data in conjunction with radiation treatment prescription.

In accordance with yet another alternative embodiment of the present invention, treatment planning process 110 does not include step 112 of generating the keV image beam and step 116 of generating the keV configuration images. Accordingly, beam source 12 can be a single energy level beam source generating radiation beam at the MeV energy level and projection detector 17 can be an image detector that is sensitive to only to the MeV radiation beam. This embodiment has an advantage of reducing the hardware complexity and the cost of radiation treatment apparatus 10 or 20. It also improves patient accessibility to the radiation treatment. In one aspect of the present invention, the tumor in patient 11 is located in a position that is unlikely to have significant movement, so the data related to its configuration stored in the radiation treatment prescription is sufficient in generating the radiation treatment plan. In another aspect of the present invention, projection detector 17 generates images of patient 11 from by the MeV radiation beam with sufficient resolutions so that they can be used for generating both configuration data and radiation absorption data. In yet another aspect, control module 18 includes algorithms for processing the MeV radiation absorption images to generate the data regarding the configuration of the tumor and the surrounding tissues in patient 11. In this aspect, the configuration data generated from the MeV images are used for deriving the radiation beam direction and shape in the radiation treatment plan.

Referring back to FIG. 3, radiation treatment planning process 110 is followed by radiation delivery process 140 in radiation treatment session 100. In accordance with one aspect of the present invention, treatment planning process 110 and radiation delivery process 140 are performed during a single radiation treatment session 100. Patient 11 remains on platform 14 throughout radiation treatment session 100. Preferably, the movement of patient 11 near the tumor under the treatment is minimized during treatment session 100. Approaches to minimize the patient movement include training patient 11 for proper breathing techniques, constraining patient 11 at suitable positions, etc. Performing treatment planning process 110 and radiation delivery process 140 in a single radiation treatment session 100 in accordance with the present invention significantly improves the precision of radiation beam projection, thereby increasing the treatment efficiency and decreasing the adverse side effects of the radiation exposure to the surrounding tissues in patient 11. It further optimizes treatment session 100 by accurately delivering the right amount of radiation to the tumor tissue. It also reduces the adverse side effect of the radiation treatment by concentrating the radiation delivery to the tumor and reducing the radiation delivered to non cancerous tissues or organs surrounding the tumor. Radiation treatment planning process 110 in accordance with the present invention can further optimize the radiation treatment plan to minimize the radiation delivered to the tissues and organs surrounding the tumor and sensitive to the radiation. All these may lead to the escalation of the prescribed radiation dose to the tumor without the deleterious effects of damaging surrounding non cancerous tissues and organs in patient 11.

Figure 5:
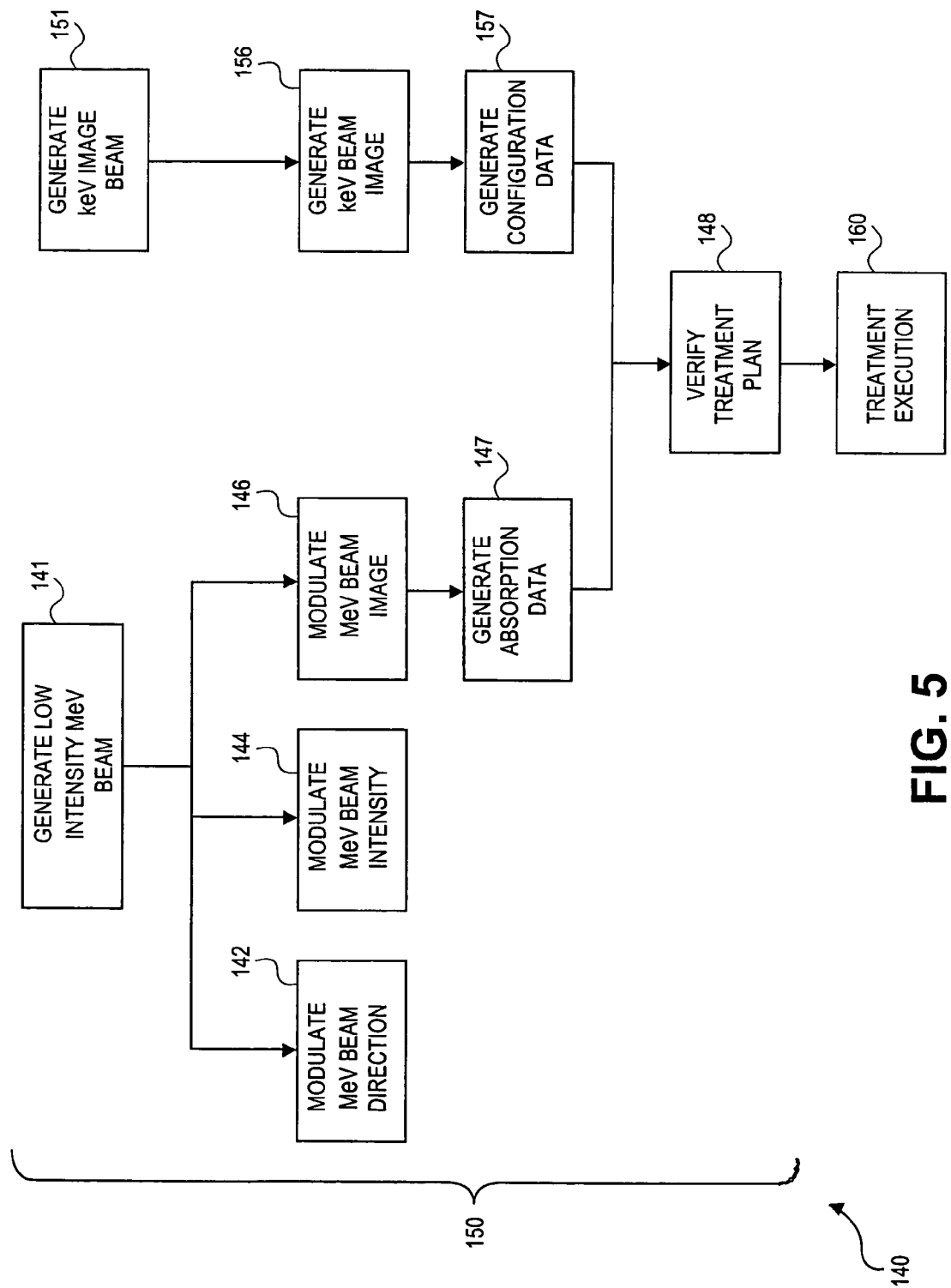
FIG. 5 illustrates a radiation delivery process in accordance with an embodiment of the present invention.

FIG. 5 is a flow chart illustrating radiation delivery process 140 in radiation treatment session 100 shown in FIG. 3. In accordance with the present invention, radiation delivery process 140 executes the radiation treatment plan generated in radiation treatment planning process 110. As shown in FIG. 5, process 140 includes a radiation treatment plan verification subprocess 150 and a radiation treatment plan execution subprocess 160.

In a step 141, beam source 12 is switched on to generate a low intensity MeV radiation beam. This beam is also referred to as a treatment plan verification beam. By example, the intensity of the MeV radiation treatment beam ranges between 1 Rad and 20 Rad. In a step 142, the direction of the MeV verification beam is modulated in accordance with the treatment plan developed in radiation treatment planning process 110 shown in FIG. 4. For example, gantry 25 (shown in FIG. 2) housing beam source 12 rotates around platform 14 to modulate the incident direction of the MeV verification beam. In a step 144, beam adjuster 16 modulates the intensity and shape of the MeV verification beam in response to the instructions from control module 18 in accordance with the radiation treatment plan.

In a step 146, projection detector 17 detects the images of tumor and the surrounding tissues in patient 11 formed by the MeV verification beam. By way of example, these images are also referred to as radiation dose verification images. In a step 147, control module 18 generates the data related to the radiation doses received or absorbed by different portions of patient 11 in response to the radiation dose verification images. In a step 148, control module 18 uses the radiation absorption data generated in step 147 to verify or evaluate the radiation treatment plan generated in radiation treatment planning process 110. A volumetric dose distribution of the treatment plan is determined using the low dose data. By way of example, these dose distribution results are also referred to as radiation dose distribution images. These low dose radiation distribution images are compared with the prescription and verified for validity. If validity is verified then full dose treatment is executed at step 160. Otherwise, further optimization and recalculation of a new treatment plan proceeds to remove differences between the measured and prescribed dose.

In accordance with an embodiment of the present invention, beam source 12 also generates a keV image beam in a step 151. In a specific aspect of the present invention, beam source 12 generates the MeV verification beam (in step 141) and the keV image beam (in step 151) as alternating pulses. In another specific aspect, beam source 12 includes two separate radiation beam sources, one for generating the MeV verification beam in step 141 and the other for generating the keV image beam in step 151. In accordance with an embodiment of the present invention, step 142 of modulating the direction of the MeV verification beam also modulates the direction of the keV image beam by rotating gantry 25 (shown in FIG. 2) around platform 14. The intensity of the keV image beam may be constant in accordance with one embodiment of the present invention.

In a step 156, projection detector 17 generates the images of patient 11 formed by the keV image beam projected on patient 11 from different directions. These images are also referred to as configuration images of the tumor and surrounding tissues in patient 11. In a step 157, control module 18 generates the data regarding the configuration of the tumor and the surrounding tissues in patient 11. The configuration data are used in step 148 in conjunction with the radiation doze data for verifying the radiation treatment plan. In accordance with an embodiment of the present invention, control module 18 can also generate a control signal to move platform 14 to reposition patient 11, thereby facilitating the focus of the radiation verification beam onto the tumor in patient 11. Repositioning the patient in a radiation therapy is described in U.S. Pat. No. 6,279,579 entitled "METHOD AND SYSTEM FOR POSITIONING PATIENTS FOR MEDICAL TREATMENT PROCEDURES" filed on Oct. 23, 1998 and issued on Aug. 28, 2001, which is incorporated herein by reference in its entirety.

Figure 6:
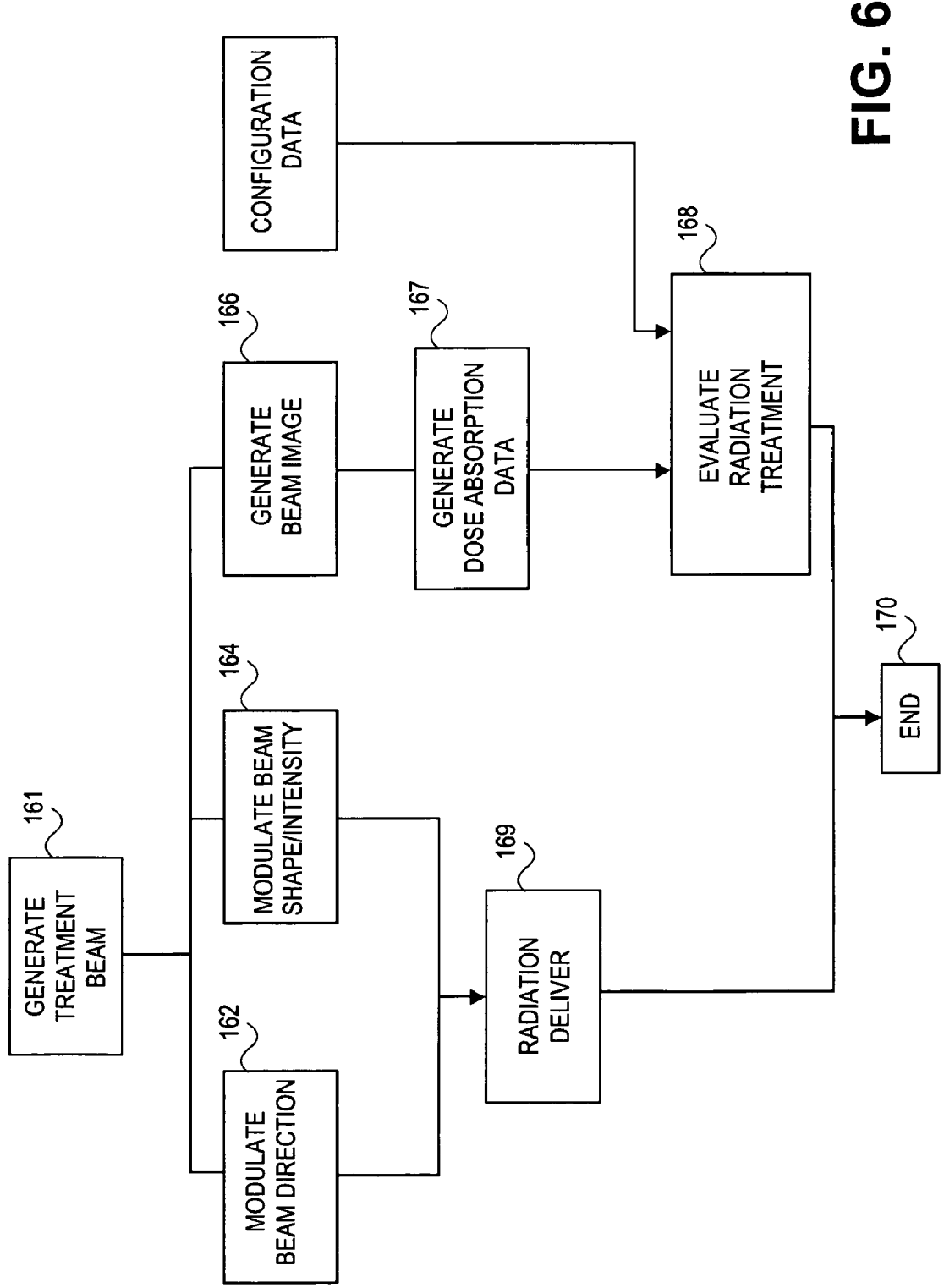
FIG. 6 illustrates radiation treatment plan execution sub-process in accordance with an embodiment of the present invention.

As shown in FIG. 5, treatment plan verification subprocess 150 is followed by radiation treatment plan execution subprocess 160. FIG. 6 illustrates radiation treatment plan execution subprocess 160. In a step 161, beam source 12 generates an MeV radiation beam at an intensity in accordance with the radiation treatment plan. This beam is also referred to as a treatment beam. By example, the intensity of the MeV radiation treatment beam ranges between 250 Rad and 1000 Rad. In a step 162, the direction of the MeV radiation treatment beam is modulated in accordance with the treatment plan. For example, gantry 25 (shown in FIG. 2) housing beam source 12 rotates around platform 14 to modulate the incident direction of the MeV treatment beam. In a step 164, beam adjuster 16 modulates the intensity and shape of the MeV treatment beam in response to the instructions from control module 18 in accordance with the radiation treatment plan.

In a step 166, projection detector 17 detects the images of tumor and the surrounding tissues in patient 11 formed by the MeV treatment beam. By way of example, these images are also referred to as radiation dose images. In a step 167, control module 18 generates the data related to the radiation doses received or absorbed by different portions of patient 11 in response to the radiation dose images. In a step 168, control module 18 uses the radiation absorption data generated in step 167 to evaluate the execution of the radiation treatment plan. A treatment dose distribution image is determined. In a step 169, the MeV treatment beam has been delivered during steps 162,164 to the tumor in patient 11 according to the radiation treatment plan and confirmed and evaluated in 167.

In accordance with an embodiment of the present invention, radiation treatment execution subprocess 160 further includes generating the keV image beam, generating the images of patient 11 formed by the keV image beam, and generating the data regarding the configuration of the tumor and the surrounding tissues in patient 11, similar to corresponding steps 151, 156, and 157 in radiation treatment verification subprocess 150 described herein above with reference to FIG. 5. In accordance with an embodiment, step 162 of modulating the direction of the MeV treatment beam also modulates the direction of the keV image beam by rotating gantry 25 (shown in FIG. 2) around platform 14. The configuration data are used in step 168 in conjunction with the radiation doze data for evaluating the radiation treatment plan execution.

In one specific embodiment of the present invention, apparatus 10 performs step 168 of evaluating radiation treatment plan execution and step 169 of delivering radiation beam to patient 11 simultaneously. In another specific embodiment, step 168 of treatment evaluation is performed during a portion of time while step 169 of treatment execution is performed.

In accordance with a particular embodiment of the present invention, control module 18 uses the configuration data to dynamically modulate the intensity, shape, and projection direction of the MeV treatment beam while delivering radiation treatment beam to the tumor in step 169. Methods for dynamically modulating radiation treatment beam in is described in U.S. patent application Ser. No. 10/037,477 entitled "METHOD AND APPARATUS FOR IRRADIATING A TARGET" and filed on Jan. 2, 2002, which is incorporated herein by reference in its entirety. In another particular embodiment of the present invention, control module 18 uses the configuration data to perform a gating process of the MeV treatment beam while performing step 169. Gating processes are described in U.S. patent application Ser. No. 09/178,383 entitled "METHOD AND SYSTEM FOR PREDICTIVE PHYSIOLOGICAL GATING OF RADIATION THERAPY" and filed on Oct. 23, 1998, U.S. patent application Ser. No. 09/712,724 entitled "METHOD AND SYSTEM FOR PHYSIOLOGICAL GATING OF RADIATION THERAPY" and filed on Nov. 14, 2000, and U.S. patent application Ser. No. 09/893,122 entitled "METHOD AND SYSTEM FOR PREDICTIVE PHYSIOLOGICAL GATING" and filed on Jun. 26, 2001, which are incorporated herein by reference in their entireties. In accordance with yet another embodiment of the present invention, control module 18 can also generate a control signal to move platform 14 to reposition the patient, thereby facilitating the focus of the radiation treatment beam onto the tumor in patient 11. Repositioning the patient in a radiation therapy is described in previously incorporated U.S. Pat. No. 6,279,579 entitled "METHOD AND SYSTEM FOR POSITIONING PATIENTS FOR MEDICAL TREATMENT PROCEDURES".

It should be noted that radiation delivery process 140 is not limited to what described herein above with reference to FIGS. 5 and 6. In accordance with an alternative embodiment of the present invention, radiation delivery process 140 does not include generating the keV image beam and generating the keV configuration images. In one aspect of the present invention, the tumor in patient 11 is located in a position that is unlikely to have significant movement. Accordingly, verifying the treatment plan in step 148 and evaluating the radiation treatment in step 168 may not need the generation of the configuration data of the tumor. In another aspect of the present invention, the movement of the tumor during radiation delivery process 140 is periodical or predictable. Furthermore, radiation treatment verification subprocess 150 is optional in accordance with the present invention. In accordance with an alternative embodiment of the present invention, radiation delivery process 140 does not include step 148 of evaluating the radiation treatment plan. Accordingly, radiation delivery process 140 also does not include steps 142, 144, and 146 described herein above and shown in FIG. 5.

The previously described system and method may be employed in various modes of therapy, such as Spiral Axial Tomotherapy (SATT), or Computed Cone Therapy (CCT).

Spiral Axial Tomotherapy (SATT). Here, a volume treatment may be produced by a sum of a series of (thin) laminar planer-dose applications (SATT projections). The dose volume may be generated by rotating the source about the patient and moving beam-lamina in an axial direction. This may be accomplished by continuously moving the patient in the axial direction, while the gantry is rotated, thereby resulting in a spiral or helical application. The SATT fan beam projections may be modulated to approximate the desired dose distribution. In another embodiment, instead of axially moving the patient, a slit formed by radiation collimating jaws may be moved in a continuous longitudinal motion.

Computed Cone Therapy (Real Time Intensity-Modulated Cone Tomotherapy). Here a volume treatment may be produced by a sum of a series of two-dimensional dose applications (CCT projections) using a modulated cone therapy beam. Each CCT projection may have axial and lateral boundaries. It may also have an associated gantry angle and possibly other angles in non-coplanar arrangements. In a simple form of CCT, the dose volume may be the result of the sum of CCT projections applied during rotation of the source about the patient. The cone may be considered as the sum of slices defined by each leaf of the multi-leaf collimator. The logical slices may be axially modulated to approximate the desired dose volume distribution. With this configuration, several modes of Tomotherapy may be performed. Note that through the dynamic use of the standard collimating jaws, the treatment may also be further optimized.

An embodiment of a procedure or protocol for performing CCT will now be described. The first part of the procedure may include a does prescription, wherein a standard tool, such as radiographs, diagnostic CT or the simulator, may be used to prescribe a dose. The prescription may be similar to that in current practice. It may include high-dose and protected-area criteria. The dose prescription may also include the selection of one or more treatment templates from a list of CCT treatment templates.

The second part of the procedure may include a CCT accelerator treatment session. During the accelerator treatment session, the prescribed treatment template may be optimized for producing the prescribed dose, and a treatment dose is applied and verified. Particularly, the accelerator treatment session may include 1) patient-setup, 2) treatment-optimization, and 3) treatment and verification.

The patient-setup and the treatment and verification steps of the accelerator treatment session may be carried out using conventional techniques. Particularly, the patient-setup in the accelerator treatment session involves positioning a patient according to the criteria of a selected template or a simulator session. Once the optimization step is completed, the treatment and verification may be carried out using procedures currently used. The entire procedure is real time in that the total accelerator time is not significantly longer than that required in performing a non-optimized treatment using the template only.

The CCT optimization procedure involves techniques and concepts similarly associated with CT imaging, Dose imaging, and "inverse CT" treatment. The product of the difference in the measured beam intensity with and without the patient and the beam-on time is the energy absorbed in a patient. That is the ergs or dose delivered by the beam along the path (line) of the beam. Thus, MeV projection data may provide information related to line integral dose. Considering a volume surrounding the radiated region, the region may be considered as composed of voxels. The dose to each voxel may be the sum of the doses received by that voxel from all the beam lines passing through that voxel during the treatment. Once dose line integral data commensurate with the number of voxels in the volume is obtained, a solvable equation may be derived and used to compute the doses to individual voxels based on the known parameters, such as the line integral data, geometry, materials properties, etc. This is very similar to CT attenuation imaging. Fan beam and cone beam reconstruction algorithms, or an ART algorithm used in CT may be used to solve the equation. Depending on how projection data is processed, either CT attenuation-images or dose-images may be reconstructed. Note that the dose images may be dependent on the incident intensity of each logical cone beam ray. This is the route of "inverse CT" treatment. It may allow a user to control the shape and magnitude of the delivered total dose to the patient. The planning for this may include computationally determining the dose line integrals of the prescribed dose and convoluting (e.g., integrating) this data with a kernel similar to that used in CT reconstruction. The result of this convolution is the desired incident beam intensity along each of the beam ray lines. The following procedure is designed to minimize the effects of, for example, beam scatter, beam build up, beam spectrum in manners similar to those used in CT imaging.

The object of optimization in CCT is to define that set of incident beam intensities along the lines, which will provide, as near as possible, the prescribed treatment-dose. In one embodiment, the optimization or treatment-optimization step in the accelerator treatment session involves acquiring a low-dose projection data (Cone Beam CT like projection data). Both low-dose keV and MeV projection data may be collected. The keV images may be used for positioning. The MeV images may be used to plan and optimize the treatment and/or to determine verification information. Since the projection image data may be obtained simultaneously during the accelerator session, there may be no requirements for image matching of either the projection images, the CT images, or Dose images which might be produced from the projection data. The projection data along with the dose prescription, the template information, and system calibration data (described below) may be used to determine a CCT treatment plan and verification criteria. The dose prescription for the treatment may include a variety of information. For example, in addition to standardized prescription data, it may also include desired dose distribution for the target, information about regions to be protected, weighting criteria, and/or limits on allowable difference between prescribed and expected dose distributions. Any or a combination of these information may be used to plan a treatment and to evaluate acceptability of a treatment template.

In one embodiment, the optimization procedure may determine the value of the incident beam intensity for each logical beam line in the cone fan and may optimize the direction and number of cones used in the treatment. A scenario for this optimization is as follows: Two pairs of low-radiation data sets are collected on the patient. Each pair may include both keV and MeV data. One pair may be obtained with open jaws, and it may include data for accurate cone beam keV and MeV reconstruction. The MeV data may also be used for dose reconstruction. The second data-set pair may be data collected using both keV and MeV, but in this case, with the jaws, multi-leaf, and gantry-angles configured based on a template. The MeV data may be used to determine a dose distribution.

Calibration data may be used in the optimization procedure. As discussed previously, the system for performing CCT may be calibrated at a desired period interval, such as every two weeks, or every month. In one embodiment, the calibration procedure may be performed by using an appropriate phantom, such as a cylindrical water phantom. A CCT treatment associated with a template designed to produce a desired dose volume is then applied to the phantom. The treatment may be defined by specifying the incident beam energy (WIBE), of each logical ray of the treatment template. After the Phantom is "treated" by the CCT treatment, the dose volume may produce a dose distribution.

During the "treatment" of the phantom, dose line integrals (WDL) may be measured and recorded. The dose distribution (WDD) may be measured with a suitable point radiation detector. Also low dose MeV (treatment beam spectrum radiation) and keV (diagnostic beam energy) open collimator projection data (M-WPD & K-WPD) may be acquired.

In the calibration procedure, tallied dose-line-integrals (T-WDL) may also be computed by summing the measured WDD along ray lines. These may be computed for the gantry angles of the template. The dose line-integrals may be calculated for logical cone beam rays covering the maximum cone beam aperture of the accelerator. The geometry of the logical cone beam rays may be the same in each cone and may be defined in the template. The logical beam rays may correspond to the rays from the source to each detector element of the detection array. The physical detector elements may be grouped to form logical detector elements and, thereby, logical cone beam rays. The WDL and T-WDL may be configured to represent the same template gantry angle and logical cone beam ray configuration. The measured integral dose WTD (the total energy deposition into the phantom) may also be determined. The dose line integrals, dose distribution, open collimator projection data, tallied dose line integrals, and/or measured integral dose may be stored as calibration data, and be made available during use of the template.

In one embodiment, the computational steps in the optimization procedure may include the following:

1) Correlate the dose prescription with the patient anatomy, which has been measured in the treatment position. This transfer of the dose position prescription from prescription space to accelerator space coordinates may be accomplished by calculating a volumetric CT image from the keV projection data, and transferring the prescribed dose information to it. The transfer may also be accomplished by transferring the information in projection space.

2) From the prescription-dose, dose line-integrals (PDL) may be computed for the gantry angles of the template. The prescription integral dose (total energy deposition), PTD, may also be determined. The computational algorithms may be similar to those used in the phantom calibration procedure, as previously described. First iteration dose line integral (DL1) (equal to {PDL−(PTD/WTD)*WDL}) may be determined. The DL1 may be convolved with an appropriate kernel to form convolved first iteration prescription dose line integrals, CPDL1.

3) The prescription treatment PIBE1 may be determined from WIBE−CPDL1. A second iteration PIBE2 may be evaluated by using the dose image through convolution and back projection of the PIBE1. From this dose image, one can determine values for a second dose line integral DL2 and dose distribution TD2. As in item 2, these may be used to determine DL2={PDL−(PTD/TD2)*DL1} and evaluate PIBE2.

4) The PIBE set defines the treatment, and may be used for treatment. Dose images and verification information may be determined from the PIBE set. If desired, low-dose MeV data may be collected using scaled PIBE values. This low-dose data may be used to calculate and compare the anticipated dose with the prescribed dose, and to evaluate the possible requirement for a different template.

In another embodiment, the dose line integrals may be determined based on the incident beam intensity and other factors, such as the functions of absorption, geometry, and beam characteristics, along the line. In this case, beam build up and beam scatter may need to be accounted for by the use of appropriate kernels in convolution and back projection. In a treatment planning, much of the calculating time relates to computing and accounting for the complications of the functions of absorption, geometry, and beam characteristics. A more accurate determination of these kernels may be obtained by use of empirical data from calibration and from keV and MeV absorption measurements made during the treatment session. In this approach, the complications of the functions may be empirically measured under the exact circumstances of treatment. In essence, many of the functions complications are "normalized" out. This may be done in a similar way that the complications of beam spectrum and detector gain are normalized out in standard CT through the use of a phantom (water or other tissue equivalent material) in CT system calibration. It is believed that performing CCT using such approach may be more accurate and be less computationally intensive than current treatment planning schemes.

By now it should be appreciated that an apparatus and a method for a radiation therapy have been provided. In accordance with one aspect of the present invention, a radiation therapy session includes a real time planning process followed by a radiation delivery process. The radiation therapy performed in accordance with the present invention is not adversely affected by the inter session changes in patient positions and tumor configurations. The real time planning process in accordance with another aspect of the present invention provides updated data regarding radiation intensity, incident direction, and duration for each radiation delivery process, thereby optimizing the radiation treatment therapy session and significantly reducing the effects of improper patient positioning, patient movement, inadequately optimized radiation prescription. The apparatus and the radiation treatment described herein are also capable of delivering accurate radiation dosages to the tumorous region in a patient, while minimizing the radiation exposure of the healthy regions of the patient under the radiation therapy.

While specific embodiments of the present invention have been described herein above, they are not intended as a limitation on the scope of the present invention. The present invention encompasses those modifications and variations of the described embodiments that are obvious to those skilled in the art. For example, the method of irradiating a target in accordance with the present invention is not limited to irradiating a tumor in a human patient. The method is equally applicable in treating other abnormal conditions. It is also applicable in veterinarian medical treatment of animals.

What is claimed:

1. A radiation method, comprising:
    illuminating an object with a first beam at a first energy level;
    determining a first image of the object formed by the first beam;
    determining configuration data using the first image;
    illuminating the object with a second beam at a second energy level;
    determining a second image of the object formed by the second beam;
    determining radiation absorption data using the second image;
    determining a radiation treatment plan using the configuration data and the radiation absorption data, wherein the radiation treatment plan is determined before or during a treatment session; and
    storing or executing the radiation treatment plan.

2. The method of claim 1, wherein the first energy level is a keV energy level, and the second energy level is a MeV energy level.

3. The method of claim 1, wherein the first beam and the second beam have low intensities.

4. The method of claim 1, wherein the first beam has an intensity between approximately 1 Rad and 20 Rad, and the second beam has an intensity between approximately 250 Rad and 1000 Rad.

5. The method of claim 1, wherein the second beam has a constant intensity during a session.

6. The method of claim 1, further comprising adjusting an intensity of the second beam during a session.

7. The method of claim 1, wherein the illuminating the object with the first beam and the illuminating the object with the second beam are performed in alternating pulses.

8. The method of claim 1, wherein the illuminating the object with the first beam and the illuminating the object with the second beam are performed sequentially.

9. The method of claim 1, wherein the determining configuration data comprises comparing data associated with the first image with data regarding configuration of the object.

10. The method of claim 1, wherein the determining radiation absorption data comprises calculating a radiation absorption rate in the object.

11. The method of claim 1, further comprising storing the configuration data and the radiation absorption data in a computer readable medium.

12. The method of claim 1, wherein the configuration data comprises one or a combination of location, size, and shape of the object.

13. The method of claim 1, wherein the radiation treatment plan is configured for use in a computed cone therapy.

14. The method of claim 1, wherein the determining the treatment plan comprises creating the treatment plan.

15. The method of claim 1, wherein the determining the treatment plan comprises modifying the treatment plan.

16. The radiation method of claim 1, wherein the treatment session is a first treatment session.

17. A radiation system, comprising:
    means for generating a first beam at a first energy level for illuminating an object;
    means for determining a first image of the object formed by the first beam;
    means for determining configuration data using the first image;
    means for generating a second beam at a second energy level for illuminating the object;
    means for determining a second image of the object formed by the second beam;
    means for determining radiation absorption data using the second image; and
    means for determining a radiation treatment plan using the configuration data and the radiation absorption data;
    wherein the means for determining the radiation treatment plan determines the radiation treatment plan before or during a treatment session.

18. The system of claim 17, wherein the means for determining configuration data comprises means for comparing data associated with the first image with data regarding configuration of the object.

19. The system of claim 17, wherein the means for determining radiation absorption data comprises means for calculating a radiation absorption rate in the object.

20. The system of claim 17, further comprising means for storing the configuration data and the radiation absorption data.

21. The method of claim 17, wherein the means for determining the treatment plan comprises means for creating the treatment plan.

22. The method of claim 17, wherein the means for determining the treatment plan comprises means for modifying the treatment plan.

23. The radiation system of claim 17, wherein the treatment session is a first treatment session.

24. A radiation method, comprising:
    illuminating an object with a beam at a MeV energy level;
    determining an image of the object formed by the beam;
    determining configuration data and radiation absorption data using the image;
    determining a radiation treatment plan based on the configuration data and the radiation absorption data; and
    storing or executing the radiation treatment plan.

25. The method of claim 24, wherein the beam has a constant intensity during a session.

26. The method of claim 24, wherein the determining radiation absorption data comprises calculating a radiation absorption rate in the object.

27. The method of claim 24, further comprising storing the configuration data and the radiation absorption data in a computer readable medium.

28. The method of claim 24, wherein the configuration data comprises one or a combination of location, size, and shape of the object.

29. The method of claim 24, wherein the radiation treatment plan is configured for use in a computed cone therapy.

30. A radiation method, comprising:
illuminating an object with a beam at a MeV energy level;
determining an image of the object formed by the beam;
determining configuration data and radiation absorption data using the image;
determining a radiation treatment plan based on the configuration data and the radiation absorption data; and
adjusting an intensity of the beam during a session.

31. A radiation method, comprising:
illuminating an object with a beam at a MeV energy level;
determining an image of the object formed by the beam;
determining configuration data and radiation absorption data using the image;
determining a radiation treatment plan based on the configuration data and the radiation absorption data, wherein the determining configuration data comprises comparing data associated with the image with data regarding configuration of the object specified in a treatment prescription; and
storing or executing the radiation treatment plan.

32. A radiation system, comprising:
means for generating a beam at a MeV energy level for illuminating an object;
means for determining an image of the object formed by the beam;
means for determining configuration data and radiation absorption data using the image; and
means for determining a radiation treatment plan using the configuration data and the radiation absorption data.

33. The system of claim 32, wherein the means for determining radiation absorption data comprises means for calculating a radiation absorption rate in the object.

34. The system of claim 32, further comprising means for storing the configuration data and the radiation absorption data.

35. A radiation system, comprising:
means for generating a beam at a MeV energy level for illuminating an object;
means for determining an image of the object formed by the beam;
means for determining configuration data and radiation absorption data using the image;
means for determining a radiation treatment plan using the configuration data and the radiation absorption data; and
means for adjusting an intensity of the beam during a session.

36. A radiation system, comprising:
means for generating a beam at a MeV energy level for illuminating an object;
means for determining an image of the object formed by the beam;
means for determining configuration data and radiation absorption data using the image; and
means for determining a radiation treatment plan using the configuration data and the radiation absorption data;
wherein the means for determining configuration data comprises means for comparing data associated with the image with data regarding configuration of the object specified in a treatment prescription.

37. A radiation process, comprising:
illuminating an object with a radiation beam at a MeV energy level;
determining an image of the object formed by the radiation beam;
determining radiation absorption data using the image;
determining a treatment plan based at least in part on the determined radiation absorption data, wherein the treatment plan is determined after the object is illuminated with the radiation beam; and
storing or executing the treatment plan.

38. The process of claim 37, further comprising determining configuration data for the object.

39. The process of claim 38, wherein the determining the configuration data comprises
illuminating the object with an image beam;
determining an image formed by the image beam; and
determining the configuration data using the image formed by the image beam.

40. The process of claim 38, wherein the treatment plan is determined based on the configuration data.

41. The process of claim 38, further comprising generating a treatment beam, and adjusting the treatment beam based on the configuration data.

42. The process of claim 41, wherein the adjusting comprises one or a combination of changing a direction, a shape, and an intensity of the treatment beam.

43. The process of claim 38, further comprising gating delivery of radiation based on the configuration data.

44. A radiation process, comprising:
illuminating an object with a radiation beam at a MeV energy level;
determining an image of the object formed by the radiation beam;
determining radiation absorption data using the image;
determining a treatment plan based at least in part on the determined radiation absorption data, wherein the treatment plan is determined after the object is illuminated with the radiation beam;
verifying the treatment plan before illuminating the object with a treatment beam; and
storing or executing the treatment plan.

45. A radiation system, comprising:
means for generating a radiation beam at a MeV energy level for illuminating an object;
means for determining an image of the object formed by the radiation beam;
means for determining radiation absorption data using the image; and
means for determining a treatment plan based at least in part on the determined radiation absorption data;
wherein the means for determining the treatment plan is configured to determine the treatment plan after the object has been illuminated by the radiation beam.

46. The system of claim 45, further comprising means for determining configuration data for the object.

47. The system of claim 46, further comprising means for gating a delivery of radiation based on the configuration data.

48. An apparatus for irradiating an object, comprising:
a platform for supporting an object;
a first beam source configured to generate a first radiation beam at a first intensity level and a second radiation beam at a second intensity level toward the platform;

a beam adjuster in front of the first beam source for adjusting a radiation beam directed from the first beam source, the beam adjuster comprising a multi-leaf collimator;

a projection detector configured to generate a first image of the object illuminated by the first radiation beam at the first intensity level;

a control module coupled to the projection detector and to the beam adjuster; and a second beam source configured to generate an image beam toward the platform, wherein the projection detector is further configured to generate a second image of the object illuminated by the image beam.

49. An apparatus for irradiating an object, comprising:

a platform for supporting an object;

a first beam source configured to generate a first radiation beam at a first intensity level and a second radiation beam at a second intensity level toward the platform;

a beam adjuster in front of the first beam source for adjusting a radiation beam directed from the first beam source, the beam adjuster comprising a multi-leaf collimator;

a projection detector configured to generate a first image of the object illuminated by the first radiation beam at the first intensity level; and a control module coupled to the projection detector and to the beam adjuster, wherein the control module is configured to control the beam adjuster to cover at least a portion of a body, and wherein the at least a portion comprises a part of a target region.

50. The apparatus of claim 49, wherein the control module is configured to develop a radiation treatment plan based on the first image.

51. The apparatus of claim 48, wherein the control module is configured to develop a radiation treatment plan based on one or both of the first image and the second image.

52. The apparatus of claim 49, wherein the control module is configured to adjust one or a combination of a shape, an intensity, and a direction of the second radiation beam.

53. The apparatus of claim 49, wherein the first image is usable in determining a treatment plan.

54. The apparatus of claim 49, wherein the control module is configured to control the beam adjuster based on data from the projection detector.

55. The apparatus of claim 49, wherein the target region comprises tissue that is to be treated.

* * * * *